US010334880B2

(12) United States Patent
(10) Patent No.: US 10,334,880 B2
(45) Date of Patent: Jul. 2, 2019

Rogers et al.

(54) AEROSOL DELIVERY DEVICE INCLUDING CONNECTOR COMPRISING EXTENSION AND RECEPTACLE

(71) Applicant: RAI Strategic Holdings, Inc., Winston-Salem, NC (US)

(72) Inventors: James William Rogers, Winston-Salem, NC (US); Steven L. Worm, Raleigh, NC (US); David G. Christopherson, Raleigh, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 192 days.

(21) Appl. No.: 15/081,485

(22) Filed: Mar. 25, 2016

(65) Prior Publication Data

US 2017/0273355 A1 Sep. 28, 2017

(51) Int. Cl.
*F17C 7/04* (2006.01)
*A61M 16/00* (2006.01)
(Continued)

(52) U.S. Cl.
CPC .......... *A24F 47/008* (2013.01); *H01R 24/58* (2013.01); *H01R 2105/00* (2013.01)

(58) Field of Classification Search
CPC ... A24F 47/008; A61M 11/042; A61M 15/06; A61M 2016/0024; A61M 2205/502;
(Continued)

(56) References Cited

U.S. PATENT DOCUMENTS 1,535,451 A * 4/1925 Cohen ..................... H01R 4/52 123/169 R
1,771,366 A 7/1930 Wyss et al.
(Continued)

FOREIGN PATENT DOCUMENTS

AU 276250 7/1965
CA 2 641 869 5/2010
(Continued)

OTHER PUBLICATIONS

International Search Report for International Application No. PCT/IB2017/051698.
(Continued)

*Primary Examiner* — Sang Y Paik
(74) *Attorney, Agent, or Firm* — Womble Bond Dickinson (US) LLP

(57) ABSTRACT

The present disclosure relates to an aerosol delivery device. The aerosol delivery device may include a control body with a first connector portion and a cartridge with a second connector portion. The first connector portion and the second connector portion may be configured to releasably engage each other. One of the first connector portion and the second connector portion may include an extension and the other of the first connector portion and the second connector portion may include a receptacle configured to receive the extension. The extension may include contact sections positioned along a longitudinal length thereof. The contact sections may be electrically insulated from one another by at least one spacer and may be configured to form an electrical connection with the receptacle. A related assembly method is also provided.

9 Claims, 9 Drawing Sheets

(51) Int. Cl.
*A24F 47/00* (2006.01)
*H01R 24/58* (2011.01)
*H01R 105/00* (2006.01)

(58) Field of Classification Search
CPC ...... A61M 2205/581; A61M 2205/582; A61M 2205/587; A61M 2205/8206; A61M 2205/8237; H05B 1/0297; H05B 3/44; H01R 2105/00; H01R 24/58; H01R 24/00; H01R 24/20; H01R 24/38; F22B 1/284
USPC .................................................. 392/386–406
See application file for complete search history.

(56) References Cited

U.S. PATENT DOCUMENTS 2,057,353 A 10/1936 Whittemore, Jr.
2,104,266 A 1/1938 McCormick
3,200,819 A 8/1965 Gilbert
4,284,089 A 8/1981 Ray
4,303,083 A 12/1981 Burruss, Jr.
4,735,217 A 4/1988 Gerth et al.
4,848,374 A 7/1989 Chard et al.
4,907,606 A 3/1990 Lilja et al.
4,922,901 A 5/1990 Brooks et al.
4,945,931 A 8/1990 Gori
4,947,874 A 8/1990 Brooks et al.
4,947,875 A 8/1990 Brooks et al.
4,986,286 A 1/1991 Roberts et al.
5,012,807 A * 5/1991 Stutz, Jr. .............. A61N 1/3752 607/37
5,019,122 A 5/1991 Clearman et al.
5,042,510 A 8/1991 Curtiss et al.
5,060,671 A 10/1991 Counts et al.
5,093,894 A 3/1992 Deevi et al.
5,144,962 A 9/1992 Counts et al.
5,249,586 A 10/1993 Morgan et al.
5,261,424 A 11/1993 Sprinkel, Jr.
5,322,075 A 6/1994 Deevi et al.
5,353,813 A 10/1994 Deevi et al.
5,369,723 A 11/1994 Counts et al.
5,372,148 A 12/1994 McCafferty et al.
5,388,574 A 2/1995 Ingebrethsen et al.
5,408,574 A 4/1995 Deevi et al.
5,468,936 A 11/1995 Deevi et al.
5,498,850 A 3/1996 Das
5,515,842 A 5/1996 Ramseyer et al.
5,530,225 A 6/1996 Hajaligol
5,564,442 A 10/1996 MacDonald et al.
5,649,554 A 7/1997 Sprinkel et al.
5,666,977 A 9/1997 Higgins et al.
5,687,746 A 11/1997 Rose et al.
5,726,421 A 3/1998 Fleischhauer et al.
5,727,571 A 3/1998 Meiring et al.
5,743,251 A 4/1998 Howell et al.
5,799,663 A 9/1998 Gross et al.
5,819,756 A 10/1998 Mielordt
5,865,185 A 2/1999 Collins et al.
5,865,186 A 2/1999 Volsey, II
5,878,752 A 3/1999 Adams et al.
5,894,841 A 4/1999 Voges
5,934,289 A 8/1999 Watkins et al.
5,954,979 A 9/1999 Counts et al.
5,967,148 A 10/1999 Harris et al.
6,040,560 A 3/2000 Fleischhauer et al.
6,053,176 A 4/2000 Adams et al.
6,089,857 A 7/2000 Matsuura et al.
6,095,153 A 8/2000 Kessler et al.
6,125,853 A 10/2000 Susa et al.
6,155,268 A 12/2000 Takeuchi
6,164,287 A 12/2000 White
6,196,218 B1 3/2001 Voges
6,196,219 B1 3/2001 Hess et al.
6,439,933 B1 * 8/2002 Moji ...................... H01R 24/58 439/668
6,598,607 B2 7/2003 Adiga et al.
6,601,776 B1 8/2003 Oljaca et al.
6,615,840 B1 9/2003 Fournier et al.
6,688,313 B2 2/2004 Wrenn et al.
6,715,494 B1 * 4/2004 McCoy ..................... A24F 5/00 128/202.21
6,772,756 B2 8/2004 Shayan
6,803,545 B2 10/2004 Blake et al.
6,854,461 B2 2/2005 Nichols
6,854,470 B1 2/2005 Pu
7,117,867 B2 10/2006 Cox et al.
7,293,565 B2 11/2007 Griffin et al.
7,513,253 B2 4/2009 Kobayashi et al.
7,775,459 B2 8/2010 Martens, III et al.
7,832,410 B2 11/2010 Hon
7,845,359 B2 12/2010 Montaser
7,896,006 B2 3/2011 Hamano et al.
8,127,772 B2 3/2012 Montaser
8,314,591 B2 11/2012 Terry et al.
8,365,742 B2 2/2013 Hon
8,402,976 B2 3/2013 Fernando et al.
8,499,766 B1 8/2013 Newton
8,528,569 B1 9/2013 Newton
8,550,069 B2 10/2013 Alelov
8,851,081 B2 10/2014 Fernando et al.
8,910,639 B2 12/2014 Chang et al.
2002/0146242 A1 10/2002 Vieira
2003/0226837 A1 12/2003 Blake et al.
2004/0118401 A1 6/2004 Smith et al.
2004/0129280 A1 7/2004 Woodson et al.
2004/0200488 A1 10/2004 Felter et al.
2004/0226568 A1 11/2004 Takeuchi et al.
2005/0016550 A1 1/2005 Katase
2006/0016453 A1 1/2006 Kim
2006/0196518 A1 9/2006 Hon
2007/0074734 A1 4/2007 Braunshteyn et al.
2007/0102013 A1 5/2007 Adams et al.
2007/0215167 A1 9/2007 Crooks et al.
2008/0085103 A1 4/2008 Beland et al.
2008/0092912 A1 4/2008 Robinson et al.
2008/0257367 A1 10/2008 Paterno et al.
2008/0276947 A1 11/2008 Martzel
2008/0302374 A1 12/2008 Wengert et al.
2009/0095311 A1 4/2009 Hon
2009/0095312 A1 4/2009 Herbrich et al.
2009/0126745 A1 5/2009 Hon
2009/0188490 A1 7/2009 Hon
2009/0230117 A1 9/2009 Fernando et al.
2009/0272379 A1 11/2009 Thorens et al.
2009/0283103 A1 11/2009 Nielsen et al.
2009/0320863 A1 12/2009 Fernando et al.
2010/0043809 A1 2/2010 Magnon
2010/0083959 A1 4/2010 Siller
2010/0200006 A1 8/2010 Robinson et al.
2010/0229881 A1 9/2010 Hearn
2010/0242974 A1 9/2010 Pan
2010/0307518 A1 12/2010 Wang
2010/0313901 A1 12/2010 Fernando et al.
2011/0005535 A1 1/2011 Xiu
2011/0011396 A1 1/2011 Fang
2011/0036363 A1 2/2011 Urtsev et al.
2011/0036365 A1 2/2011 Chong et al.
2011/0094523 A1 4/2011 Thorens et al.
2011/0126848 A1 6/2011 Zuber et al.
2011/0155153 A1 6/2011 Thorens et al.
2011/0155718 A1 6/2011 Greim et al.
2011/0168194 A1 7/2011 Hon
2011/0265806 A1 11/2011 Alarcon et al.
2011/0309157 A1 12/2011 Yang et al.
2012/0042885 A1 2/2012 Stone et al.
2012/0060853 A1 3/2012 Robinson et al.
2012/0111347 A1 5/2012 Hon
2012/0132643 A1 5/2012 Choi et al.
2012/0227752 A1 9/2012 Alelov
2012/0231464 A1 9/2012 Yu et al.
2012/0260927 A1 10/2012 Liu
2012/0279512 A1 11/2012 Hon
2012/0318882 A1 12/2012 Abehasera
2013/0037041 A1 2/2013 Worm et al.

(56) References Cited

U.S. PATENT DOCUMENTS

| | | | |
|---|---|---|---|
| 2013/0056013 | A1 | 3/2013 | Terry et al. |
| 2013/0081625 | A1 | 4/2013 | Rustad et al. |
| 2013/0081642 | A1 | 4/2013 | Safari |
| 2013/0192619 | A1 | 8/2013 | Tucker et al. |
| 2013/0255702 | A1 | 10/2013 | Griffith, Jr. et al. |
| 2013/0306084 | A1 | 11/2013 | Flick |
| 2013/0319439 | A1 | 12/2013 | Gorelick et al. |
| 2013/0340750 | A1 | 12/2013 | Thorens et al. |
| 2013/0340775 | A1 | 12/2013 | Juster et al. |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0109921 | A1 | 4/2014 | Chen |
| 2014/0157583 | A1 | 6/2014 | Ward et al. |
| 2014/0209105 | A1 | 7/2014 | Sears et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak, III et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2014/0345631 | A1 | 11/2014 | Bowen et al. |
| 2015/0007838 | A1 | 1/2015 | Fernando et al. |
| 2015/0053217 | A1 | 2/2015 | Steingraber et al. |
| 2015/0068542 | A1 | 3/2015 | Chang et al. |
| 2015/0245658 | A1* | 9/2015 | Worm .................. A24F 47/008 131/328 |
| 2016/0007653 | A1 | 1/2016 | Tu |
| 2016/0037826 | A1 | 2/2016 | Hearn et al. |

FOREIGN PATENT DOCUMENTS

| | | | |
|---|---|---|---|
| CN | 1541577 | | 11/2004 |
| CN | 2719043 | | 8/2005 |
| CN | 200997909 | | 1/2008 |
| CN | 101116542 | | 2/2008 |
| CN | 101176805 | | 5/2008 |
| CN | 201379072 | | 1/2010 |
| CN | 203353683 | U | 12/2013 |
| DE | 10 2006 004 484 | | 8/2007 |
| DE | 102006041042 | | 3/2008 |
| DE | 20 2009 010 400 | | 11/2009 |
| EP | 0 295 122 | | 12/1988 |
| EP | 0 430 566 | | 6/1991 |
| EP | 0 845 220 | | 6/1998 |
| EP | 1 618 803 | | 1/2006 |
| EP | 2 316 286 | | 5/2011 |
| EP | 2888964 | A1 | 7/2015 |
| GB | 2469850 | | 11/2010 |
| WO | WO 1997/48293 | | 12/1997 |
| WO | WO 2003/034847 | | 5/2003 |
| WO | WO 2004/043175 | | 5/2004 |
| WO | WO 2004/080216 | | 9/2004 |
| WO | WO 2005/099494 | | 10/2005 |
| WO | WO 2007/078273 | | 7/2007 |
| WO | WO 2007/131449 | | 11/2007 |
| WO | WO 2009/105919 | | 9/2009 |
| WO | WO 2009/155734 | | 12/2009 |
| WO | WO 2010/003480 | | 1/2010 |
| WO | WO 2010/045670 | | 4/2010 |
| WO | WO 2010/073122 | | 7/2010 |
| WO | WO 2010/118644 | | 10/2010 |
| WO | WO 2010/140937 | | 12/2010 |
| WO | WO 2011/010334 | | 1/2011 |
| WO | WO 2012/072762 | | 6/2012 |
| WO | WO 2012/100523 | | 8/2012 |
| WO | WO 2013/089551 | | 6/2013 |
| WO | 2015042809 | A1 | 4/2015 |

OTHER PUBLICATIONS

"Connectors", CUI Inc., http://www.cui.com/catalog/components/connectors, Retrieved Mar. 25, 2016.

"Jacks & Plugs", Switchcraft, http://www.switchcraft.com/category.aspx?Parent=3, Retrieved Mar. 25, 2016.

Mill-Max, https://www.mill-max.com/product_finder/1, Retrieved Mar. 25, 2016.

"Spring Probe Connectors", Smiths Connectors, http://www.smithconnectors.com/us/products/spring-probe-connectors, Retrieved Mar. 25, 2016.

* cited by examiner

AEROSOL DELIVERY DEVICE INCLUDING CONNECTOR COMPRISING EXTENSION AND RECEPTACLE

BACKGROUND

Field of the Disclosure

The present disclosure relates to aerosol delivery devices such as electronic cigarettes, and more particularly to connectors for aerosol delivery devices including an atomizer, and associated systems and apparatuses. The atomizer may be configured to heat an aerosol precursor composition, which may be made or derived from tobacco or otherwise incorporate tobacco, to form an inhalable substance for human consumption.

Description of Related Art

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., and U.S. Pat. App. Pub. No. 2015/0059780 to Davis et al., which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

However, some aerosol delivery device may include multiple pieces, which may be separable. For example, aerosol delivery devices may include a control body and a cartridge. Accordingly, aerosol delivery devices may include couplers that allow for coupling and decoupling of the cartridge and the control body, such that the cartridge may be refilled or replaced. However, such connectors may wear out from repeated usage, may be difficult to engage or disengage, or may provide unreliable electrical connections. Thus, advances with respect to connectors for aerosol delivery devices may be desirable.

BRIEF SUMMARY OF THE DISCLOSURE

The present disclosure relates to assembly of cartridges for aerosol delivery devices configured to produce aerosol and which aerosol delivery devices, in some embodiments, may be referred to as electronic cigarettes. As described in detail herein, embodiments of connectors for aerosol delivery devices are disclosed. For example, in one aspect, an aerosol delivery device is provided. The aerosol delivery device may include a control body including an electrical power source and a first connector portion. The aerosol delivery device may additionally include a cartridge. The cartridge may include a reservoir configured to contain an aerosol precursor composition, an atomizer configured to heat the aerosol precursor composition received from the reservoir to produce an aerosol, and a second connector portion. The first connector portion and the second connector portion may be configured to releasably engage each other. One of the first connector portion and the second connector portion may include an extension and the other of the first connector portion and the second connector portion may include a receptacle configured to receive the extension. The extension may include a plurality of contact sections positioned along a longitudinal length thereof. The contact sections may be electrically insulated from one another by at least one spacer and may be configured to form an electrical connection with the receptacle.

In some embodiments the contact sections may include a data contact section configured to form a data connection between the cartridge and the control body. The air inlet may be defined in the cartridge. The first connector portion may define a pressure port configured to be in fluid communication with the air inlet when the first connector portion engages the second connector portion.

In some embodiments the first connector portion may further include an O-ring configured to engage an inner surface of the second connector portion. The extension may include a detent and the receptacle may include a flexible member configured to engage the detent to retain the connection between the first connector portion and the second connector portion. The extension may include a tip-ring-sleeve plug. The receptacle may include a center pin terminal. The extension and the receptacle may be centrally disposed with respect to a respective one of the first connector portion and the second connector portion. The extension may be configured to engage the receptacle regardless of a relative rotational position of the cartridge with respect to the control body.

In an additional aspect, a method for assembling an aerosol delivery device is provided. The method may include forming a control body by inserting an electrical power source into a control body outer body and engaging a first connector portion with the control body outer body. Additionally, the method may include forming a cartridge by inserting a reservoir and an atomizer into a cartridge outer body and engaging a second connector portion with the cartridge outer body. The reservoir may be configured to contain an aerosol precursor composition and the atomizer may be configured to heat the aerosol precursor composition received from the reservoir to produce an aerosol. The first connector portion and the second connector portion may be configured to releasably engage each other. One of the first connector portion and the second connector portion may include an extension and the other of the first connector portion and the second connector portion may include a receptacle configured to receive the extension. The extension may include a plurality of contact sections positioned along a longitudinal length thereof. The contact sections may be electrically insulated from one another by at least one spacer and may be configured to form an electrical connection with the receptacle.

In some embodiments engaging the first connector portion with the control body outer body may include engaging a coupler with a flow tube and engaging the flow tube with the control body outer body. Engaging the second connector portion with the cartridge outer body may include engaging a base with the cartridge outer body. Forming the control body may further include engaging an O-ring with the coupler. The O-ring may be configured to engage an inner surface of the second connector portion.

In some embodiments forming the control body may further include inserting a flow sensor in the control body outer body. The coupler may define a pressure port configured to be in fluid communication with the cartridge when the first connector portion engages the second connector portion. The method may additionally include engaging a pressure tube with the flow sensor and with the coupler.

In some embodiments the method may further include engaging the extension with one of the coupler and the base and engaging the receptacle with the other of the coupler and the base. Engaging the extension with one of the coupler and the base and engaging the receptacle with the other of the coupler and the base may include centrally disposing the extension and the receptacle with respect to a respective one of the coupler and the base. Engaging the extension with one of the coupler and the base may include engaging a tip-ring-sleeve plug with one of the coupler and the base. Additionally, the method may include inserting a controller into the control body outer body and inserting an electronic control component into the cartridge outer body. The method may further include electrically coupling a data contact section of the extension with one of the controller and the electronic control component.

These and other features, aspects, and advantages of the disclosure will be apparent from a reading of the following detailed description together with the accompanying drawings, which are briefly described below.

BRIEF DESCRIPTION OF THE FIGURES

Figure 1:
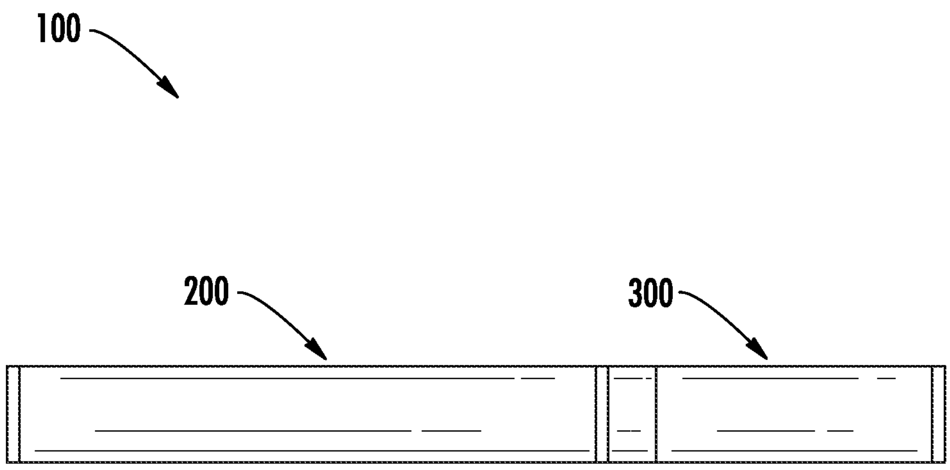
Figure 2:
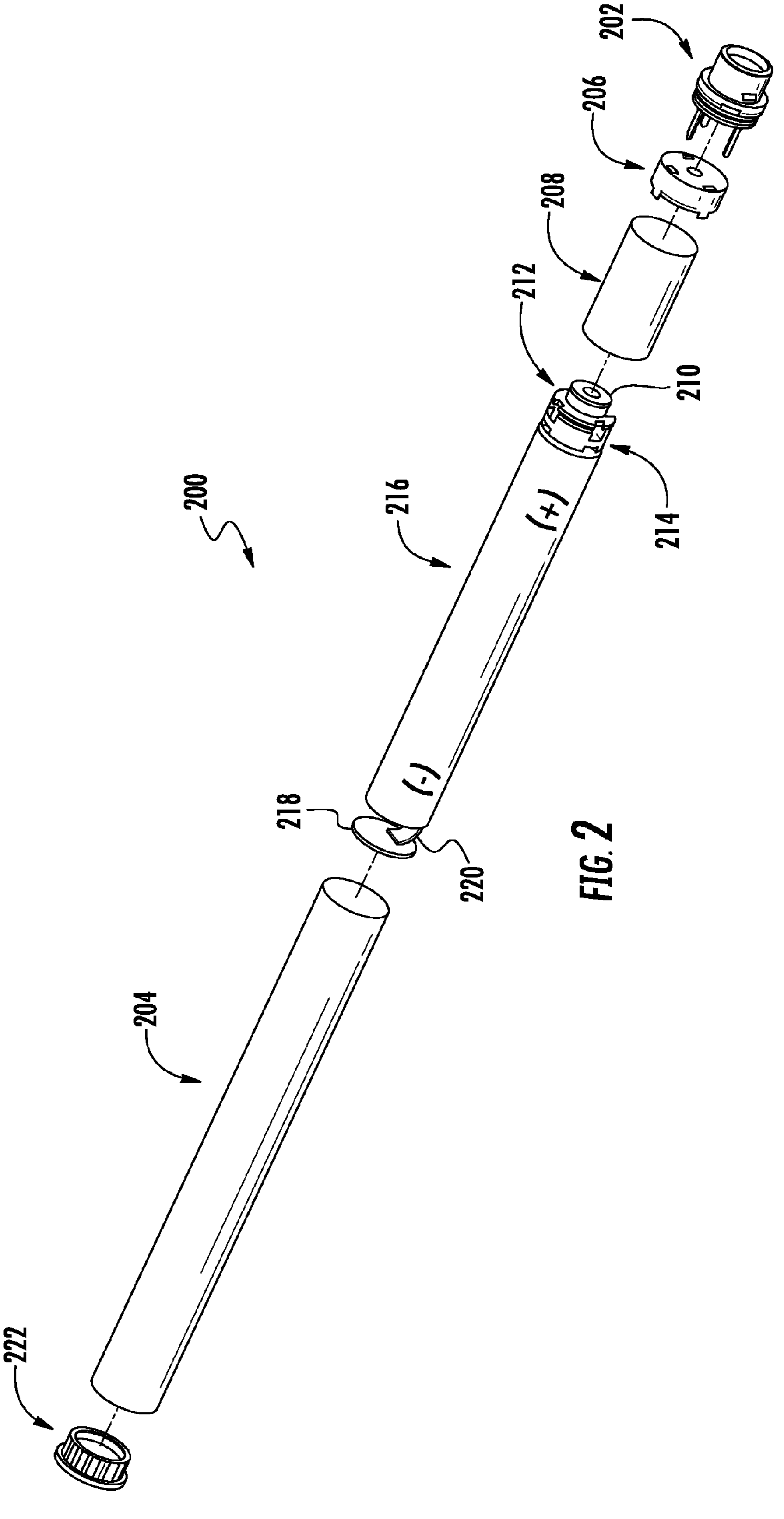
Figure 3:
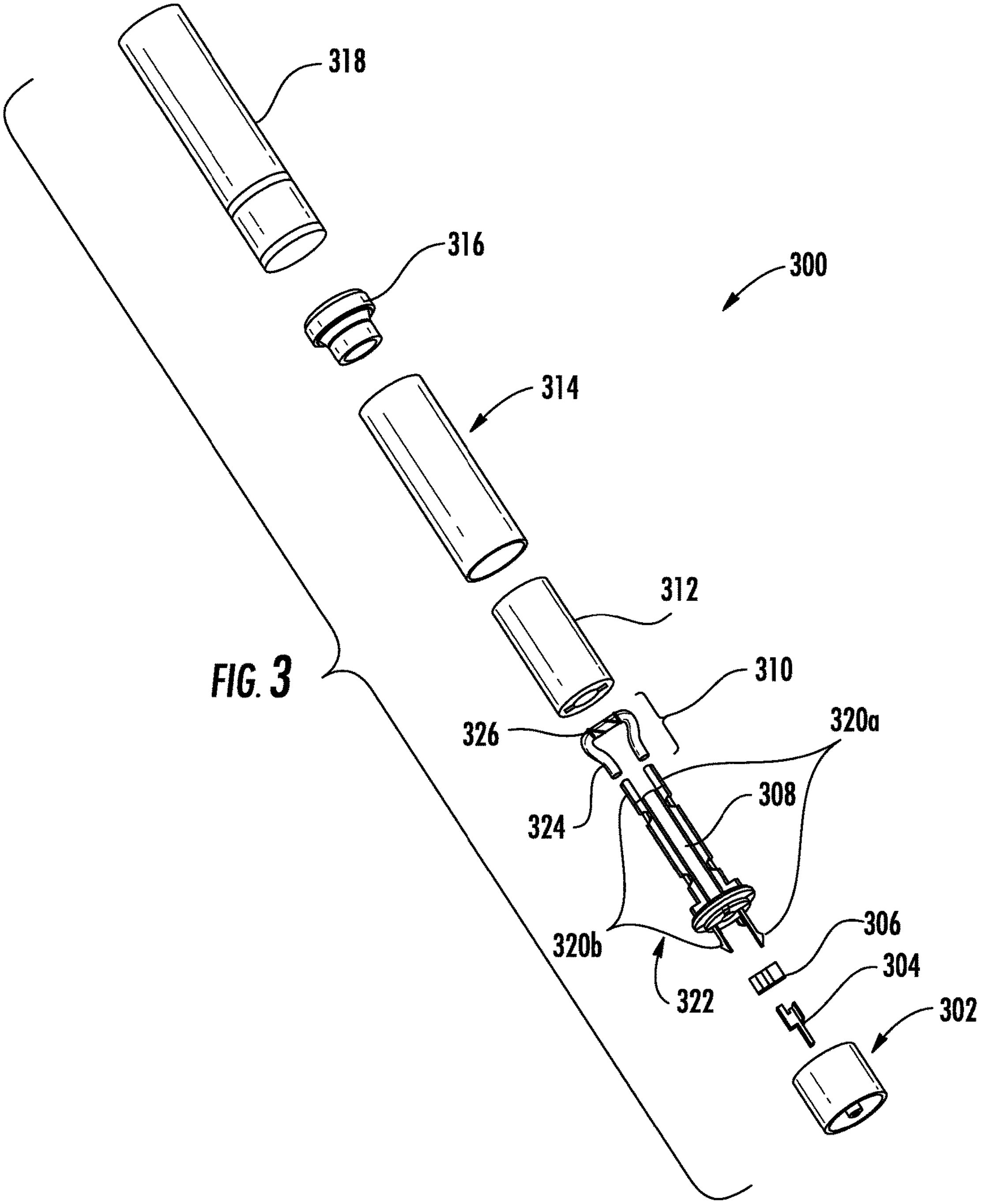
Figure 4:
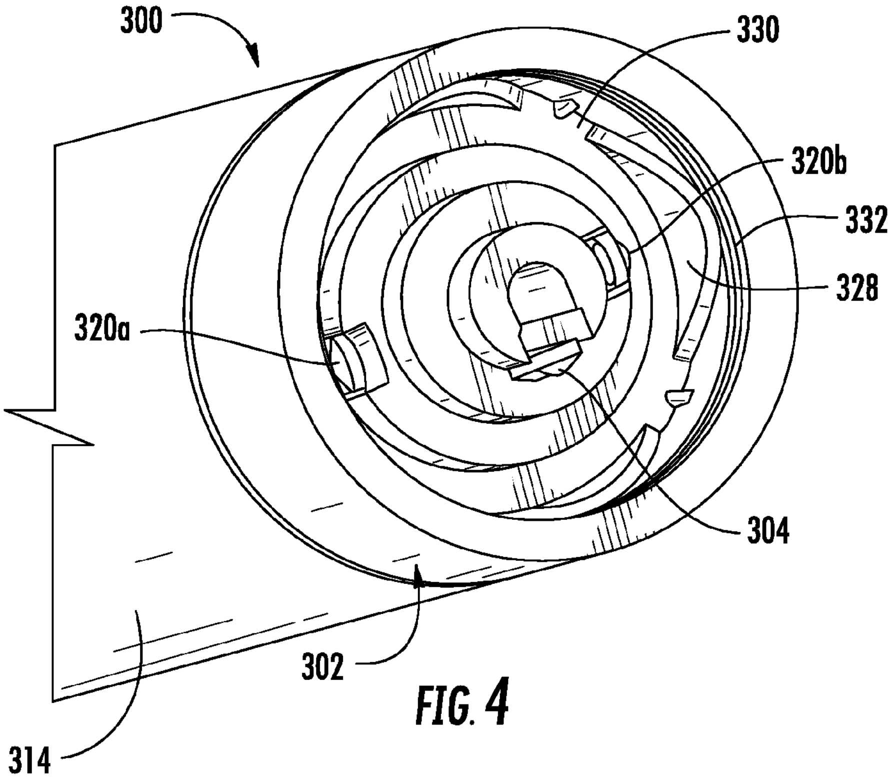
Figure 5:
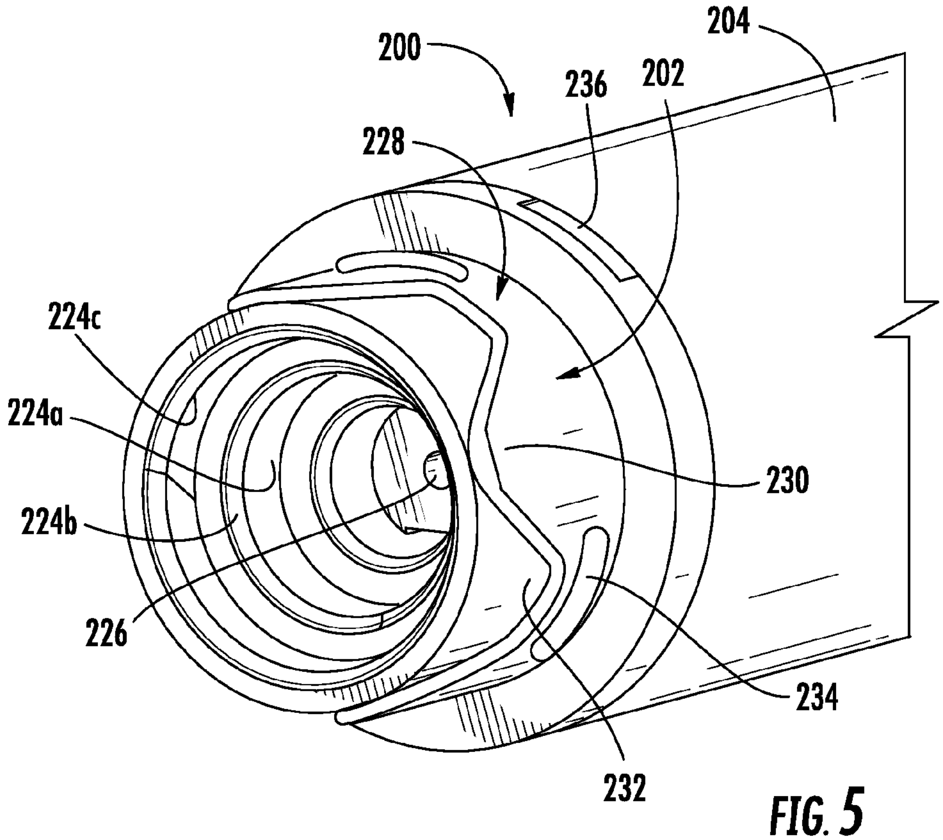
Figure 6:
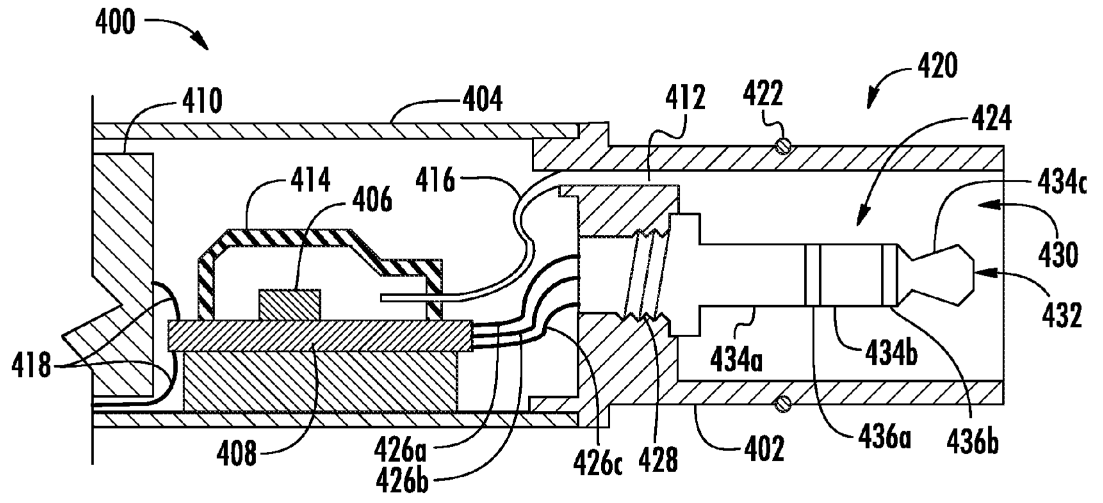
Figure 7:
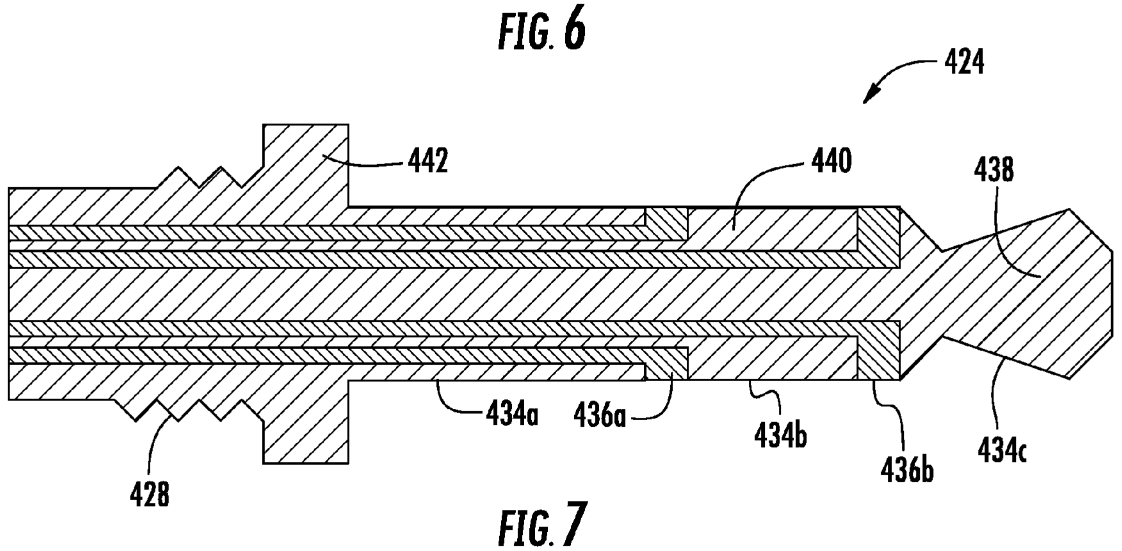
Figure 8:
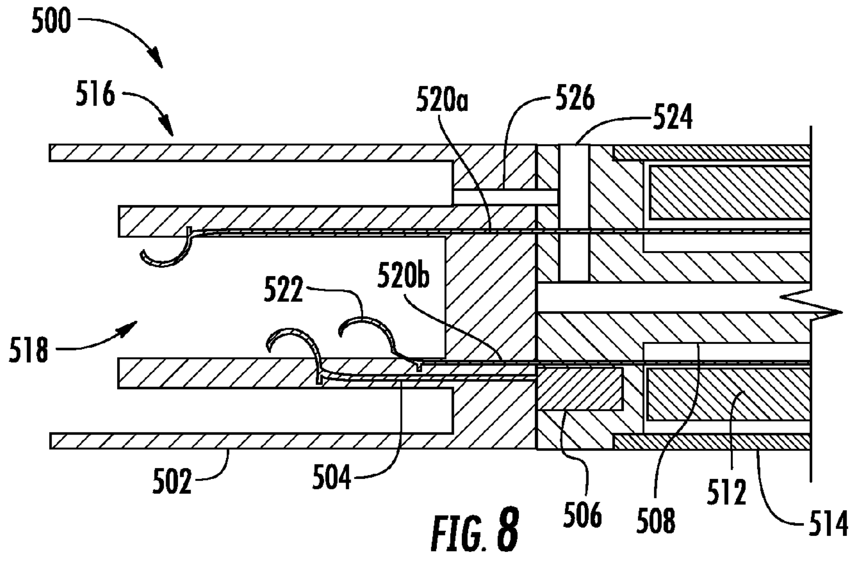
Figure 9:
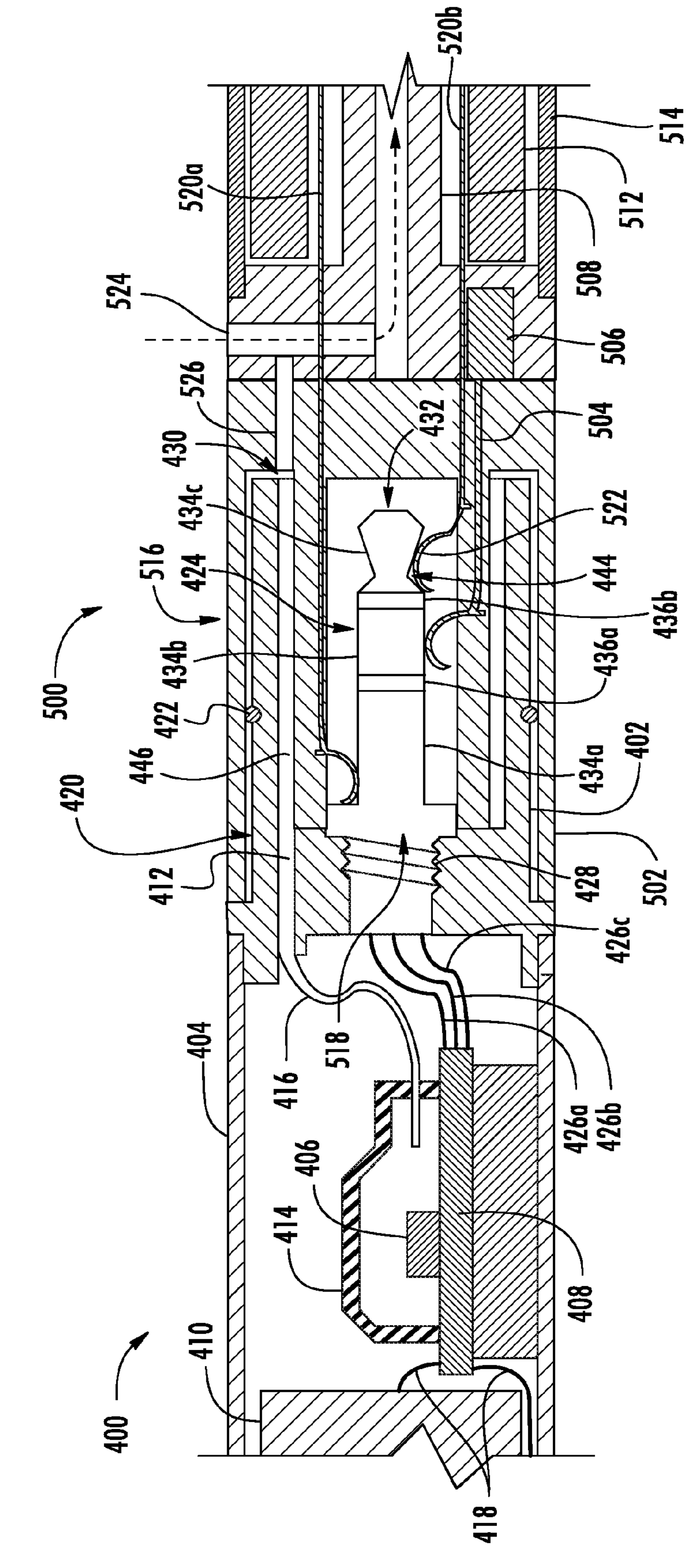
Figure 10:
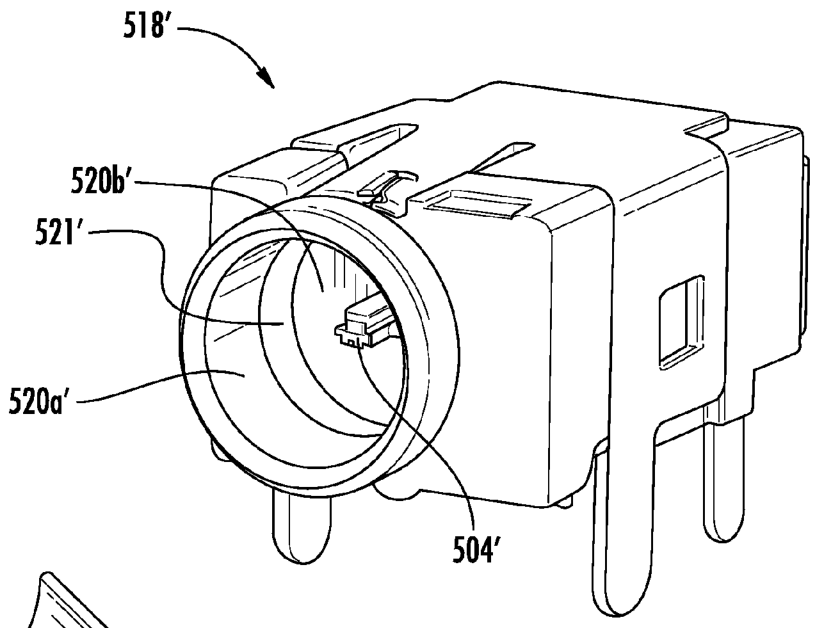
Figure 11:
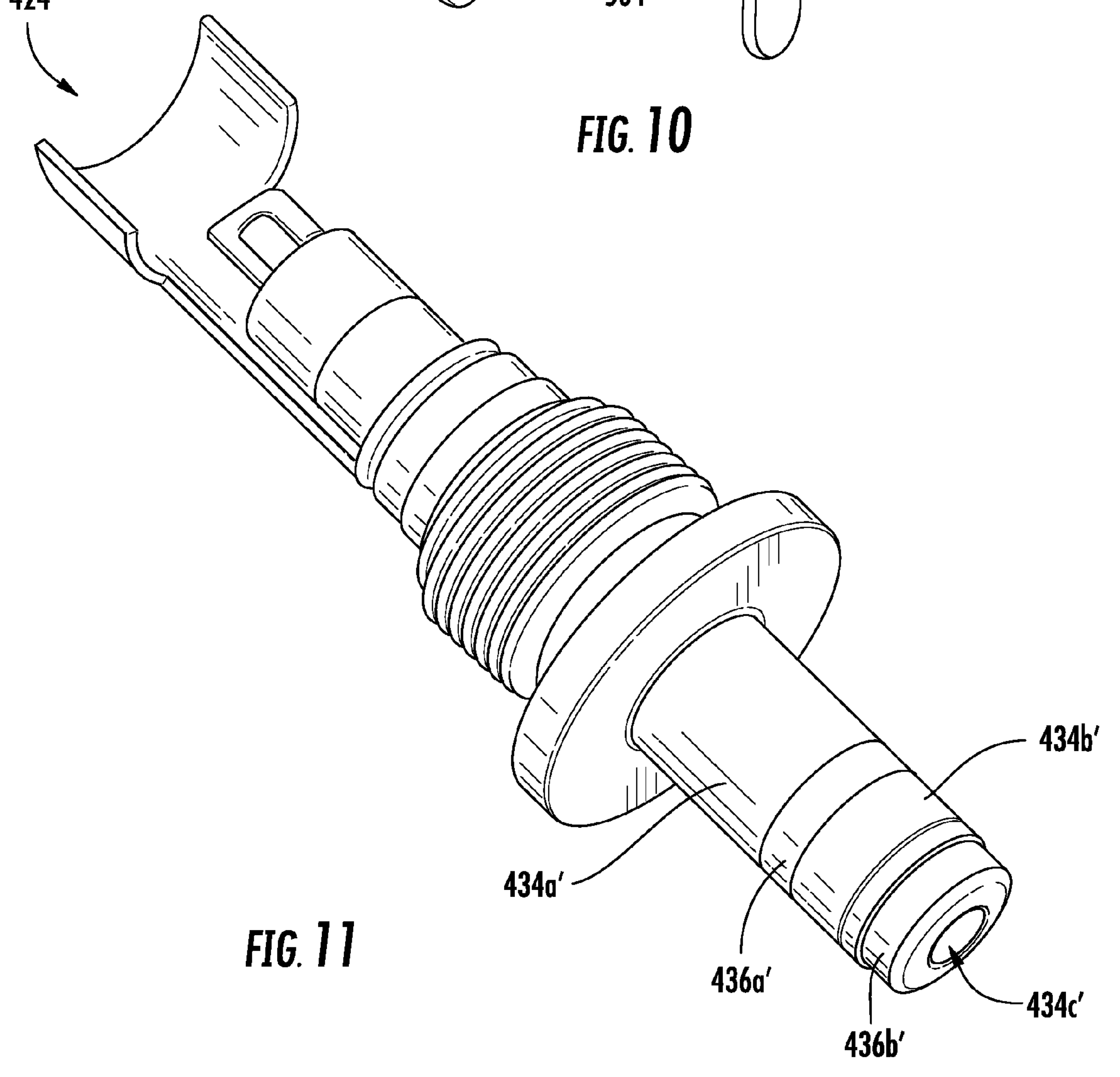
Figure 12:
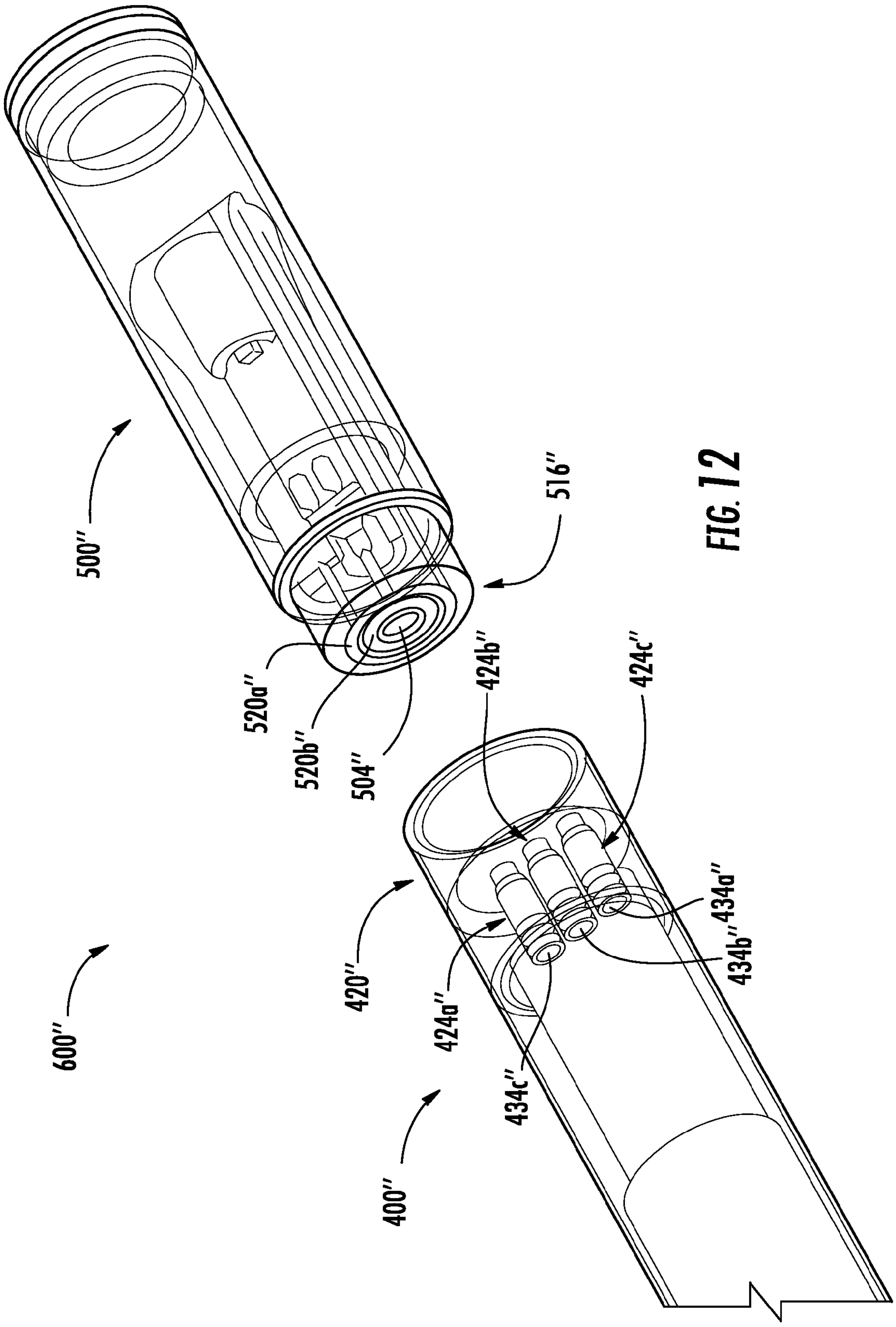
Figure 13:
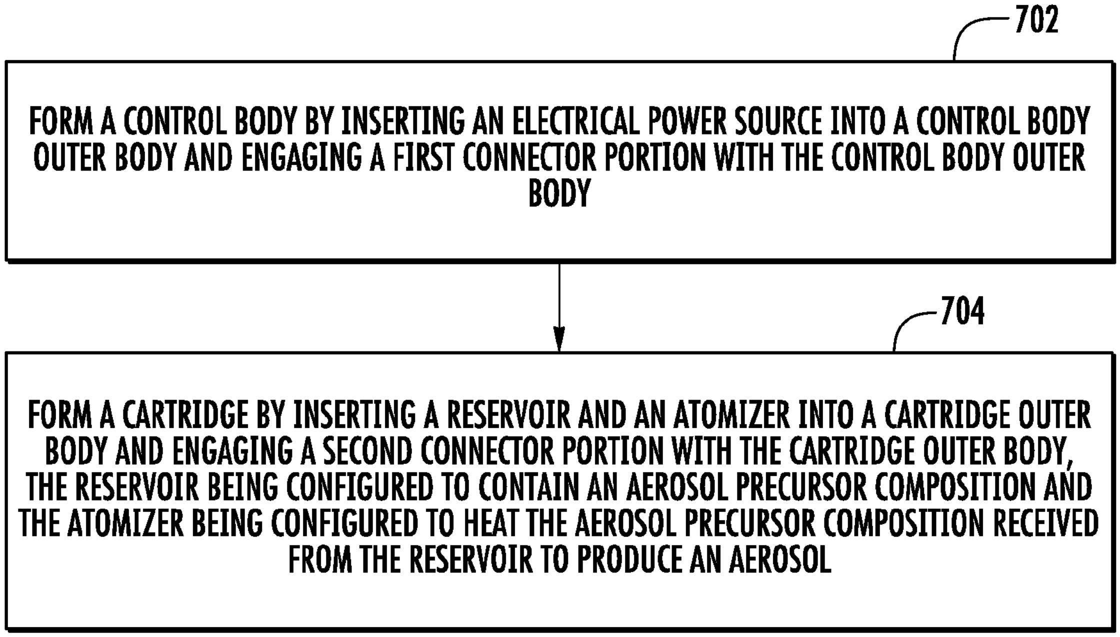

Having thus described the disclosure in the foregoing general terms, reference will now be made to the accompanying drawings, which are not necessarily drawn to scale, and wherein:

FIG. 1 illustrates a side view of an aerosol delivery device comprising a cartridge and a control body in an assembled configuration according to an example embodiment of the present disclosure;

FIG. 2 illustrates the control body of FIG. 1 in an exploded configuration according to an example embodiment of the present disclosure;

FIG. 3 illustrates the cartridge of FIG. 1 in an exploded configuration according to an example embodiment of the present disclosure;

FIG. 4 illustrates an end view of a base of the cartridge of FIG. 1 according to an example embodiment of the present disclosure;

FIG. 5 illustrates an end view of a coupler of the control body of FIG. 1 according to an example embodiment of the present disclosure;

FIG. 6 illustrates a partial modified sectional view through a control body including a first connector portion according to an example embodiment of the present disclosure;

FIG. 7 illustrates a sectional view through an extension of the first connector portion of FIG. 6 according to an example embodiment of the present disclosure;

FIG. 8 illustrates a partial sectional view through a cartridge including a second connector portion according to an example embodiment of the present disclosure;

FIG. 9 illustrates a partial modified sectional view through an aerosol delivery device including the control body of FIG. 6 and the cartridge of FIG. 8 according to an example embodiment of the present disclosure;

FIG. 10 illustrates a perspective view of a receptacle including a center pin according to an example embodiment of the present disclosure;

FIG. 11 illustrates a perspective view of an extension configured to engage the receptacle of FIG. 10 according to an example embodiment of the present disclosure;

FIG. 12 illustrates a perspective view of an aerosol delivery device including a plurality of spring pins and a corresponding receptacle according to an example embodiment of the present disclosure; and FIG. 13 schematically illustrates a method for assembling an aerosol delivery device according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of systems for assembling aerosol delivery devices. The aerosol delivery devices may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized as an electronic smoking article such as an electronic cigarette or "e-cigarette."

While the systems are generally described herein in terms of embodiments associated with aerosol delivery devices such as so-called "e-cigarettes," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery mechanisms by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Smoking articles of the present disclosure generally include a number of components provided within an outer shell or body. The overall design of the outer shell or body can vary, and the format or configuration of the outer body that can define the overall size and shape of the smoking article can vary. Typically, an elongated body resembling the shape of a cigarette or cigar can be a formed from a single, unitary shell; or the elongated body can be formed of two or more separable pieces. For example, a smoking article can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one embodiment, all of the components of the smoking article are contained within one outer body or shell. Alternatively, a smoking article can comprise two or more shells that are joined and are separable. For example, a smoking article can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various smoking article designs and component arrangements can be appreciated upon consideration of the commercially available electronic smoking articles.

Aerosol delivery devices of the present disclosure most preferably comprise some combination of a power source (i.e., an electrical power source), at least one controller (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

One example embodiment of an aerosol delivery device 100 is illustrated in FIG. 1. In particular, FIG. 1 illustrates an aerosol delivery device 100 including a control body 200 and a cartridge 300. The control body 200 and the cartridge 300 can be permanently or detachably aligned in a functioning relationship. Various connectors may connect the cartridge 300 to the control body 200 to result in a threaded engagement, a press-fit engagement, an interference fit, a magnetic engagement, or the like. The aerosol delivery device 100 may be substantially rod-like, substantially tubular shaped, or substantially cylindrically shaped in some embodiments when the cartridge 300 and the control body 200 are in an assembled configuration. However, various other configurations such as rectangular or fob-shaped may be employed in other embodiments.

In specific embodiments, one or both of the cartridge 300 and the control body 200 may be referred to as being disposable or as being reusable. For example, the control body 200 may have a replaceable battery or a rechargeable battery and/or a capacitor and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 300 may comprise a single-use cartridge, as disclosed in U.S. Pat. No. 8,910,639 to Change et al., which is incorporated herein by reference in its entirety.

FIG. 2 illustrates an exploded view of the control body 200 of the aerosol delivery device 100 according to an example embodiment of the present disclosure. As illustrated, the control body 200 may comprise a coupler 202, an outer body 204 (i.e., a control body outer body), a sealing member 206, an adhesive member 208 (e.g., KAPTON® tape), a flow sensor 210 (e.g., a puff sensor or pressure switch), a controller 212, a spacer 214, an electrical power source 216 (e.g., a battery, which may be rechargeable), a circuit board with an indicator 218 (e.g., a light emitting diode (LED)), a connector circuit 220, and an end cap 222. Examples of electrical power sources are described in U.S. Pat. App. Pub. No. 2010/0028766 by Peckerar et al., the disclosure of which is incorporated herein by reference in its entirety.

With respect to the flow sensor 210, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. App. Pub. No. 2014/0270727 to Ampolini et al., which is incorporated herein by reference in its entirety.

In one embodiment the indicator 218 may comprise one or more light emitting diodes. The indicator 218 can be in communication with the controller 212 through the connector circuit 220 and be illuminated, for example, during a user drawing on a cartridge coupled to the coupler 202, as detected by the flow sensor 210. The end cap 222 may be adapted to make visible the illumination provided thereunder by the indicator 218. Accordingly, the indicator 218 may be illuminated during use of the aerosol delivery device 100 to simulate the lit end of a smoking article. However, in other embodiments the indicator 218 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and materials or components that may be used in the present article are disclosed in U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

FIG. 3 illustrates the cartridge 300 in an exploded configuration. As illustrated, the cartridge 300 may comprise a base 302, a control component terminal 304, an electronic control component 306, a flow director 308, an atomizer 310, a reservoir substrate 312, an outer body 314 (i.e., a cartridge outer body), a mouthpiece 316, a label 318, and first and second heating terminals **320*a*, 320*b*** according to an example embodiment of the present disclosure.

In some embodiments the first and second heating terminals **320*a*, 320*b* may be embedded in, or otherwise coupled to, the flow director 308. For example, the first and second heating terminals 320*a*, 320*b* may be insert molded in the flow director 308. Accordingly, the flow director 308 and the first and second heating terminals may be collectively referred to as a flow director assembly 322. Additional description with respect to the first and second heating terminals 320***a*, 320*b* and the flow director 308 is provided in U.S. Pat. Pub. No. 2015/0335071 to Brinkley et al., which is incorporated herein by reference in its entirety.

The atomizer 310 may comprise a liquid transport element 324 and a heating element 326. The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. Pat. No. 9,220,302 to DePiano et al., which is incorporated herein by reference in its entirety.

The base 302 may be coupled to a first end of the outer body 314 and the mouthpiece 316 may be coupled to an opposing second end of the outer body to substantially or fully enclose other components of the cartridge 300 therein. For example, the electronic control component 306, the flow director 308, the atomizer 310, and the reservoir substrate 312 may be substantially or entirely retained within the outer body 314. The label 318 may at least partially surround the outer body 314, and optionally the base 302, and include information such as a product identifier thereon. The base 302 may be configured to engage the coupler 202 of the control body 200 (see, e.g., FIG. 2). In some embodiments the base 302 may comprise anti-rotation features that substantially prevent relative rotation between the cartridge and the control body as disclosed in U.S. Pat. App. Pub. No. 2014/0261495 to Novak et al., which is incorporated herein by reference in its entirety.

A reservoir may be configured to retain the aerosol precursor composition. For example, as described above, the reservoir may comprise the reservoir substrate 312. However, the reservoir may comprise any other embodiment of a container or a material configured to hold an aerosol precursor composition.

Representative types of aerosol precursor components and formulations are also set forth and characterized in U.S. Pat. No. 7,726,320 to Robinson et al.; U.S. Pat. No. 8,881,737 to Collett et al.; and U.S. Pat. No. 9,254,002 to Chong et al., and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Embodiments of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; and U.S. Pat. No. 8,627,828 to Strickland et al.; as well as US Pat. Pub. Nos. 2010/0018539 to Brinkley et al. and 2010/0170522 to Sun et al.; and PCT WO 97/06786 to Johnson et al., all of which are incorporated by reference herein.

The reservoir substrate 312 may comprise a plurality of layers of nonwoven fibers formed into the shape of a tube encircling the interior of the outer body 314 of the cartridge 300. Thus, liquid components, for example, can be sorptively retained by the reservoir substrate 312. The reservoir substrate 312 is in fluid connection with the liquid transport element 324. Thus, the liquid transport element 324 may be configured to transport liquid from the reservoir substrate 312 to the heating element 326 via capillary action or other liquid transport mechanism.

As illustrated, the liquid transport element 324 may be in direct contact with the heating element 326. As further illustrated in FIG. 3, the heating element 326 may comprise a wire defining a plurality of coils wound about the liquid transport element 324. In some embodiments the heating element 326 may be formed by winding the wire about the liquid transport element 324 as described in U.S. Pat. No. 9,210,738 to Ward et al., which is incorporated herein by reference in its entirety. Further, in some embodiments the wire may define a variable coil spacing, as described in U.S. Pat. App. Pub. No. 2014/0270730 to DePiano et al., which is incorporated herein by reference in its entirety. Various embodiments of materials configured to produce heat when electrical current is applied therethrough may be employed to form the heating element 326. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials, and ceramic (e.g., a positive or negative temperature coefficient ceramic).

However, various other embodiments of methods may be employed to form the heating element 326, and various other embodiments of heating elements may be employed in the atomizer 310. For example, a stamped heating element may be employed in the atomizer, as described in U.S. Pat. App. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various embodiments, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

The first heating terminal 320*a* and the second heating terminal 320*b* (e.g., negative and positive heating terminals) are configured to engage opposing ends of the heating element 326 and to form an electrical connection with the control body 200 (see, e.g., FIG. 2) when the cartridge 300 is connected thereto. Further, when the control body 200 is coupled to the cartridge 300, the electronic control component 306 may form an electrical connection with the control body through the control component terminal 304. The control body 200 may thus employ the controller 212 (see, FIG. 2) to determine whether the cartridge 300 is genuine and/or perform other functions in conjunction with the electronic control component 306. Further, various examples of electronic control components and functions performed thereby are described in U.S. Pat. App. Pub. No. 2014/0096781 to Sears et al., which is incorporated herein by reference in its entirety.

Accordingly, the heating terminals 320*a*, 320*b* and the control component terminal 304 may be employed to form connections with the control body 200 (see, e.g., FIG. 2). For example, FIG. 4 illustrates an enlarged end view of the cartridge 300 at the base 302. As illustrated, the first heating terminal 320*a*, the second heating terminal 320*b*, and the control component terminal 304 may extend to exposed positions within the base 302. Thereby, the heating terminals 320*a*, 320*b* and the control component terminal 304 may be positioned for engagement with the control body 200.

By way of example, FIG. 5 illustrates an end view of the control body 200 at the coupler 202. As illustrated, the control body 200 may include a plurality of electrical contacts 224*a-c* respectively configured to contact the end of the control component terminal 304 and the ends of the heater terminals 320*a*, 320*b* (see, FIG. 3). The electrical contacts 224*a-c* may be positioned at differing radial distances from a central opening 226 through the coupler 202 and positioned at differing depths within the coupler. The depth and radius of each of the electrical contacts 224*a-c* is configured such that the end of the control component terminal 304 and the ends of the heater terminals 320*a*, 320*b* respectively come into contact therewith when the base 302 (see, FIG. 3) and the coupler 202 are joined together to establish an electrical connection therebetween.

In the illustrated embodiment the electrical contacts 224*a-c* comprise circular metal bands of varying radii positioned at differing depths within the coupler 202 as described above. Each of the bands defines a major contact surface facing radially inwardly toward the central axis of the coupler 202. The bands defining the electrical contacts 224*a-c* are separated from one another by stepped surfaces of the body of the coupler 202, which may be oriented perpendicularly to the radially facing major surfaces of the electrical contacts.

As illustrated in FIG. 5, the coupler 202 may further comprise an anti-rotation mechanism 228 configured to prevent rotation of the control body 200 relative to the cartridge 300 (see, e.g., FIG. 3) when engaged therewith. The anti-rotation mechanism 228 may comprise a plurality of protrusions 230 and a plurality of recesses 232 alternatingly disposed about an outer periphery of the coupler 202. As further illustrated in FIG. 5, a width of each of the protrusions 230 may increase from the connector end of the coupler 202 toward the outer body 204. Conversely, a width of each of the recesses 232 may decrease from the connector end of the coupler 202 toward the outer body 204.

As illustrated in FIG. 4, the base 302 of the cartridge 300 may include protrusions 328 and recesses 330. Thereby, when the base 302 is received inside the coupler 202 (see, e.g., FIG. 5), the protrusions 328 and the recesses 330 of the base may respectively engage the recesses 232 and the protrusions 230 (see, FIG. 5) of the coupler. Accordingly, when the base 302 of the cartridge 300 engages the coupler 202 of the control body 200 (see, e.g., FIG. 2), relative rotation between the control body and the base may be resisted.

As illustrated in FIG. 4, the base 302 of the cartridge 300 may further include a groove 332. Additionally, as illustrated in FIG. 5, the coupler 202 of the control body 200 may include one or more circumferential protrusions 234. The circumferential protrusions 234 may engage the groove 332 to thereby provide releasable interlocking between the cartridge 300 and the control body 200 which may resist decoupling of the cartridge from the control body. Various other details with respect to the components configured for coupling the cartridge and the control body, are provided, for example, in U.S. Pat. App. Pub. No. 2014/0261495 to DePiano et al., which is incorporated herein by reference in its entirety.

During use, a user may draw on the mouthpiece 316 of the cartridge 300 of the aerosol delivery device 100 (see, FIG. 1). This may pull air through an air inlet in the control body 200 (see, e.g., FIG. 2) or in the cartridge 300. For example, as illustrated in FIG. 5, in one embodiment an air inlet 236 may be defined between the coupler 202 and the outer body 204 of the control body 200 (see, e.g., FIG. 2), as described in U.S. Pat. No. 9,220,302 to DePiano et al., which is incorporated herein by reference in its entirety. However, the flow of air may be received through other parts of the aerosol delivery device 100 in other embodiments. As noted above with respect to FIG. 3, in some embodiments the cartridge 300 may include the flow director 308. The flow director 308 may be configured to direct the flow of air received from the control body 200 to the heating element 326 of the atomizer 310.

A sensor in the aerosol delivery device 100 (e.g., the flow sensor 210 in the control body 200; see FIG. 2) may sense the puff. When the puff is sensed, the control body 200 may direct current to the heating element 326 through a circuit including the first heating terminal 320*a* and the second heating terminal 320*b*. Accordingly, the heating element 326 may vaporize the aerosol precursor composition directed to an aerosolization zone from the reservoir substrate 312 by the liquid transport element 324. Thus, the mouthpiece 316 may allow passage of air and entrained vapor (i.e., the components of the aerosol precursor composition in an inhalable form) from the cartridge 300 to a consumer drawing thereon.

Various other details with respect to the components that may be included in the cartridge 300 are provided, for example, in U.S. Pat. Pub. No. 2015/0335071 to Brinkley et al., which is incorporated herein by reference in its entirety. Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In another embodiment substantially the entirety of the cartridge may be formed from one or more carbon materials, which may provide advantages in terms of biodegradability and absence of wires. In this regard, the heating element may comprise carbon foam, the reservoir substrate may comprise carbonized fabric, and graphite may be employed to form an electrical connection with the power source and the controller. An example embodiment of a carbon-based cartridge is provided in U.S. Pat. App. Pub. No. 2013/0255702 to Griffith et al., which is incorporated herein by reference in its entirety.

As noted above, some embodiments of aerosol delivery devices include multiple pieces (e.g., a cartridge and a control component), which may releasably engage one another. As further described above, the cartridge may include terminals that engage electrical contacts comprising circular metal bands at the control body. However, connectors defining this configuration may suffer from certain detriments.

For example, coupling of the control body to the cartridge may displace the terminals from their initial positions such that reliable connections may not be established. Further, the circular metal bands may shift out of position or wear over time such that a reliable connection may not be established. Additionally, the coupler of the control body may wear at the circumferential protrusions and/or the base of the cartridge may wear at the groove such that the security of the interlocking connection between the cartridge and the control body may be adversely affected. In this regard, the coupler and/or the base may comprise plastic materials, which may be prone to wear from repeated use. Further, when the groove and/or the circumferential protrusions wear such that the mechanical interlocking between the cartridge and the control body is adversely affected, the electrical connection between the terminals of the cartridge and the electrical contacts of the control body may also be adversely affected. Accordingly, wear on the mechanical connector portions of the aerosol delivery device may detrimentally affect both the mechanical and electrical connecting characteristics of the aerosol delivery device.

Thus, the present disclosure is directed to alternative embodiments of aerosol delivery devices including connectors that may avoid some or all of the problems noted above. The aerosol delivery devices described hereinafter may include some or all of the components of the aerosol delivery devices described above. Accordingly, for brevity purposes each of the components of the aerosol delivery device described hereinafter may not be described or illustrated where the components described above, or components substantially corresponding to the components described above, may be employed.

In this regard, FIG. 6 illustrates a partial, modified, sectional view through a control body 400 according to an embodiment of the present disclosure. As noted above, many of the components of the control body 400 may be the same as, or substantially the same as, the components of the control body 200, and hence all of the components of the control body 400 are not shown or discussed in detail. In this regard, the control body 200 may include, amongst other components, a coupler 402, an outer body 404 (i.e., a control body outer body), a flow sensor 406, a controller 408, and an electrical power source 410.

The flow sensor 406 may be configured to detect a pressure drop associated with a draw on a cartridge when such a cartridge is connected thereto. In this regard, the flow sensor 406 may be in fluid communication with a pressure port 412 defined by the coupler 402. The pressure port 412 may be in fluid communication with an air inlet. For example, in the illustrated embodiment a pressure seal 414 seals around the flow sensor 406 and connects to a pressure tube 416 that is in fluid communication with the pressure port at the coupler 402. Thereby, when the control body 400 engages a cartridge, the flow sensor 406 may be in fluid communication with an air inlet, which may be defined in the cartridge, to detect a puff on the cartridge.

The controller 408 may be electrically coupled to the electrical power source 410. For example, a plurality of battery wires 418 or other electrical connectors may connect the controller 408 to the electrical power source 410. Accordingly, the controller 408 may receive power from the electrical power source 410, which can then be directed to a cartridge to produce an aerosol.

In this regard, the control body 400 may include a first connector portion 420, which may be configured to engage a cartridge as described below. The first connector portion 420 may include the coupler 402. Additionally, the first connector portion 420 may include a seal such as an O-ring 422. The O-ring 422 may be positioned at an outer surface of the coupler 402 in order to engage a cartridge as described below.

Further, the first connector portion 420 may include an extension 424. The extension 424 may be electrically coupled to the controller 408 via a plurality of extension wires 426*a-c* or other electrical connectors. The extension 424 may be engaged with the coupler 402. For example, the extension 424 may include a threaded section 428 which may screw into the coupler 402. In this regard, the extension 424 may extend in an inner cavity 430 defined by the coupler 402.

As illustrated, in some embodiments an outer tip 432 of the extension 424 may terminate in the inner cavity 430 defined by the coupler 402. Positioning the outer tip 432 of the extension 424 in the inner cavity 430 may protect the extension from damage and protect a user from contact with the extension. However, in other embodiments the extension may extend out of the inner cavity, or the coupler may not define an inner cavity and the extension may extend from the end of the coupler.

As illustrated, the extension 424 may include a plurality of contact sections 434*a-c* at the outer surface thereof. The contact section 434*a-c* may be configured to form an electrical connection with a cartridge, as described below. The contact sections 434*a-c* may be positioned (e.g., spaced apart) along a longitudinal length of the extension 424. In this regard, the contact sections 434*a-c* may be electrically insulated from one another. For example, the contact sections 434*a-c* may be electrically insulated from one another by one or more spacers 436*a*, 436*b*. The spacers 436*a*, 436*b* may comprise an electrically insulating material such as plastic.

Whereas FIG. 6 illustrates a side view of the extension 424, FIG. 7 illustrates an enlarged sectional view through the extension 424 in order to show the components thereof. As illustrated, the third contact section 434*c* may be defined by an inner contact 438, which may extend centrally through the extension 424 along a longitudinal axis thereof. The second spacer 436*b* may extend over a portion of the inner contact 438 such that the third contact section 434*c* is exposed. A middle contact 440 may define the second contact portion 434*b*. The inner contact 438 may extend through the middle contact 440 with the second spacer 436*b* positioned therebetween to prevent the inner contact and the middle contact from contacting one another. An outer contact 442 may define the first contact section 434*a*. The inner contact 438, the middle contact 440, and the spacers 436*a*, 436*b* may extend through the outer contact 442. The first spacer 436*a* may be positioned between the outer contact 442 and the middle contact 440 to prevent contact therebetween. Accordingly, each of the contacts 438, 440, 442 may be electrically insulated from each other.

FIG. 8 illustrates a partial, modified, sectional view through a cartridge 500 according to an embodiment of the present disclosure. The cartridge 500 may include some or all of the components of the cartridge 300 (see, e.g., FIG. 3) described above. Many of the components of the cartridge 500 may be the same as, or substantially the same as, the components of the cartridge 300, and hence all of the components of the cartridge 500 are not shown or discussed in detail. In this regard, the cartridge 500 may include, amongst other components, a base 502, a control component terminal 504, an electronic control component 506, a flow director 508, a reservoir (e.g., a reservoir substrate 512), and an outer body 514 (i.e., a cartridge outer body). The cartridge 500 may additionally include an atomizer, which may be substantially similar or identical to the atomizer 310 (see, e.g., FIG. 3), a mouthpiece, which may be substantially similar or identical to the mouthpiece 316 (see, e.g., FIG. 3), and a label, which may be substantially similar or identical to the label 318 (see, e.g., FIG. 3).

As described below, the cartridge 500 may be configured to engage the control body 400 (see, e.g., FIG. 6) to form an electrical connection therewith. In this regard, the cartridge 500 may include a second connector portion 516, which may be configured to engage the first connector portion 420 of the control body 400 (see, e.g., FIG. 6). The second connector portion 516 may include the base 502. The second connector portion 516 may directly or indirectly engage the outer body 514. For example, in the illustrated embodiment the flow tube 508 directly engages the outer body 514, and the second connector portion 516 is engaged with the flow tube. In another embodiment the coupler and the flow tube may comprise an integral component that engages the outer body.

The second connector portion 516 may include a receptacle 518. The receptacle 518 may be configured to receive the extension 424 of the first connector portion 420 (see, FIG. 6) therein. Thereby, the receptacle 518 may establish an electrical connection with the extension 424. In this regard, the receptacle 518 may include the coupler 502 and a plurality of terminals.

In particular, the receptacle 518 of the second connector portion 516 may comprise a first heating terminal 520*a* and a second heating terminal 520*b*. The heating terminals 520*a*, 520*b* may be electrically coupled to the heating element of the atomizer. Further, as noted above, in some embodiments the second connector portion 516 may include the control component terminal 504. The control component terminal 504 may be electrically coupled to the electronic control component 506.

FIG. 9 illustrates a partial, modified, sectional view through an aerosol delivery device 600 including the control body 400 of FIG. 6 and the cartridge 500 of FIG. 8. As illustrated, the first connector portion 420 and the second connector portion 516 may be configured to releasably engage each other. In this regard, the base 502 of the cartridge 500 may engage the coupler 402 of the control body 400. For example, the coupler 402 of the control body 400 may be received in the base 502 of the cartridge 500. In some embodiments one of the coupler and the base may include more circumferential protrusions (see, e.g., circumferential protrusions 234 in FIG. 5) and the other of the coupler and the base may include a groove (see, e.g., grooves 332 in FIG. 4) configured to engage the one or more circumferential protrusions. Thereby, mechanical interlocking may be provided by the protrusions and the groove. Further, in some embodiments the coupler and the base may include anti-rotation mechanisms as described above to thereby prevent relative rotation between the cartridge and the control body, which may reduce wear on the various connection mechanisms.

In some embodiments the extension 424 may be configured to engage the receptacle 518 regardless of a relative rotational position of the cartridge 500 with respect to the control body 400. For example, as illustrated, the extension 424 and the receptacle 518 may be centrally disposed with respect to a respective one of the first connector portion 420 and the second connector portion 516. For example, the extension 424 and the receptacle 518 may be respectively aligned with central longitudinal axes of the control body 400 and the cartridge 500. Thereby, a user may couple the cartridge 500 to the control body 400 without rotationally aligning the cartridge and the control body to expedite attachment thereof.

Further, the cartridge 500 may electrically couple to the control body 400 when the first and second connector portions 420, 516 engage one another. In this regard, as the base 502 of the cartridge 500 engages the coupler 402 of the control body 400, the extension 424 may be received in the receptacle 518. When the extension 424 is received in the receptacle 518, the heating terminals 520*a*, 520*b* and the control component terminal 504 may engage the extension. The first heating terminal 520*a*, the second heating terminal 520*b*, and the control component terminal 504 may contact differing sections of the extension 424. In the illustrated embodiment the first heating terminal 520*a* engages the first contact section 434*a* of the extension 424, the control component terminal 504 engages the second contact section 434*b* of the extension, and the second heating terminal 520*b* engages the third contact section 434*c* of the extension. However, various other configurations may be employed in other embodiments.

In some embodiments one or more of the terminals 520*a*, 520*b*, 504 may mechanically interlock with the extension 424. In this regard, mechanical interlocking between one or more of the terminals 520*a*, 520*b*, 504 and the extension 424 may provide an improved connection between the cartridge 500 and the control body 400 and may provide a satisfying connected feel to a user. For example, the extension 424 may comprise an inwardly recessed detent 444 and the receptacle 518 may comprise a flexible member configured to engage the detent to retain the connection between the first connector portion 420 and the second connector portion 516. In this regard, in the illustrated embodiment the second heating terminal 520*b* comprises an end tab 522 configured to resiliently press into the detent 444. In some embodiments mechanical interlocking between one or more of the terminals and the extension may be provided in combination with mechanical interlocking between the base and the coupler as described above, which may further provide a secure connection feel that may be desirable to a user. In other embodiments mechanical interlocking between one or more of the terminals and the extension may be provided as an alternative to interlocking between the base and the coupler.

As noted above, each of the contact sections 434*a-c* at the extension 424 may be electrically insulated from one another by the spacers 436*a*, 436*b*. Thereby, separate electrical connections may be formed between the first heating terminal 520*a* and the first contact section 434*a*, between the control component terminal 504 and the second contact section 434*b*, and between the second heating terminal 520*b* and the third contact section 434*c*. Accordingly, the controller 408 may communicate with the electronic control component 506 to determine whether the cartridge 500 is genuine and/or perform other functions. In this regard, the second contact section 434*b* may comprise a data contact section configured to form a data connection between the cartridge 500 and the control body 400.

Further, the controller 408 may direct current to the heating element of the atomizer through the heating terminals 520*a*, 520*b* when appropriate. In this regard, the flow sensor 406 may be configured to detect a puff on the cartridge 500. When a user draws on the cartridge 500, air may be directed into the aerosol delivery device 600 through an air inlet. As illustrated, in one embodiment an air inlet 524 may be defined in the cartridge 500. For example, as illustrated, the air inlet 524 may be defined in the flow tube 508. However, in other embodiments the air inlet may be defined in the base 502, the outer body 514, or other portion of the cartridge 500.

As the air enters the cartridge 500, the flow sensor 406 may detect a pressure drop. In this regard, the pressure seal 414 seals around the flow sensor 406 and connects to a pressure tube 416 that is in fluid communication with the pressure port 412. Further, the pressure port 412 may be in fluid communication with the air inlet 524. For example, as illustrated, the pressure port 412 may extend to a cavity 446 positioned between the coupler 402 and the base 502 at an interior thereof. The cavity 446 may be substantially sealed due to the O-ring 422 or other sealing member being provided at an outer surface of the first connector portion 420 (e.g., at the outer surface of the coupler 402) and configured to engage an inner surface of the second connector portion 516 (e.g., the inner surface of the base 502) to form a seal between the base and the coupler. Additionally, the base 502 of the cartridge 500 may include a corresponding pressure port 526 that connects the cavity 446 to the air inlet 524. Thereby, the flow sensor 406 may detect a pressure drop associated with a draw on the cartridge 500 through the pressure tube 416, the pressure port 412, the cavity 446, and the corresponding pressure port 526.

Accordingly, the controller 408 may direct current through a circuit to the heating element of the atomizer in the cartridge 500. In this regard, the circuit may include one of the extension wires **426*a*, the outer contact 442 (see, FIG. 7) defining the first contact section 434*a*, the first heating terminal 520*a*, the heating element, the second heating terminal 520*b*, the inner contact 438 (see, FIG. 7) defining the third contact section 434*c*, and an additional extension wire 426*c*. Thereby, the heating element may heat the aerosol precursor composition stored in the reservoir substrate 512** or other reservoir to produce an aerosol that may be combined with the air, and which is directed to the user.

Note that configuration of the aerosol delivery device 600 described above may provide certain benefits. In this regard, the airflow to the user may be separated from the electrical connectors that join at the first and second connector portions 420, 516. In this regard, the air inlet 524 is defined in the cartridge 500 such that the air does not flow through the connection between the cartridge and the control body 400. Accordingly, any debris resulting from engagement and disengagement of the terminals **520*a*, 520*b*, 504 with the extension 424** may remain out of the airflow path.

Further, although the flow sensor 406 is in fluid communication with the air inlet 524, such fluid communication occurs along a substantially sealed path such that there is substantially no flow of air between the cartridge 500 and the control body. Additionally, the path through which the flow sensor 406 is in fluid communication with the air inlet 524 is separated from the extension 424 and the terminals **520*a*, 520*b*, 504. Thereby, any debris resulting from engagement and disengagement of the terminals 520*a*, 520*b*, 504 with the extension 424 may not be drawn to the air inlet 524**.

Further, the airflow path described above may isolate the electronic control component 506 and the controller 408 from the airflow. Thereby, issues with respect to the electronic components being damaged by moisture (e.g., by back puffs) may be avoided. This configuration also separates the electrical power source 410 from the airflow path such that issues with respect to chemicals or components of the electrical power source entering the airflow may be avoided.

Additionally, the extension 424 described above may comprise a tip-ring-sleeve plug. Tip-ring-sleeve plugs are commonly employed as audio jacks to transmit and/or receive audio. In this regard, tip-ring-sleeve plugs may be configured to endure a relatively large number of engagement and disengagement cycles.

However, the particular embodiment of the electrical connectors that may be employed in conjunction with the above-described aerosol delivery device may vary. For example, the particular configuration of the extension and the receptacle may vary. In this regard, FIG. 10 illustrates an alternate embodiment of the receptacle 518' that may be employed in the cartridge 500 of the aerosol delivery device 600. As illustrated, the receptacle 518' may include a first heating terminal **520*a*', a second heating terminal 520*b*', and a control component terminal 504'. A gap or spacer 521' may be positioned between the first and second heating terminals 520*a*', 520*b*'. The spacer 521' may comprise a material that is not electrically conductive such that the first and second heating terminals 520*a*', 520*b*' are electrically insulated from one another. As illustrated, the first and second heating terminals 520*a*', 520*b*' may comprise rings that extend about inner surfaces of the receptacle 518'. However, the control component terminal 504' may comprise a center pin terminal that extends through the center of one or both of the first and second heating terminals 520*a*', 520*b*'**.

In this regard, FIG. 11 illustrates an extension 424' that may be employed in the control body 400 in embodiments wherein the cartridge includes the receptacle 518' of FIG. 10. As illustrated, the extension 424' may include a first contact section **434*a*', a second contact section 434*b*', and a third contact section 434*c*', which may be positioned in an inner cavity. A spacer 436*a*' may be positioned between the first contact section 434*a*' and the second contact section 434*b*' to provide electrical insulation therebetween. Further, a spacer 436*b*' may be positioned between the third contact section 434*c*' and the first and/or second contact sections 434*a*', 434*b*' to provide electrical insulation therebetween. Thereby, the first and second heating terminals 520*a*', 520*b*' may respectively form electrical connections with the first and second contact sections 434*a*', 434*b*' and the control component terminal 504' may form an electrical connection with the third contact section 434*c*'**. Accordingly, in some embodiments the connector may be substantially similar to an electrical connector employed in some personal electronic devices and may include some or all of the benefits of the tip-ring-sleeve plug described above.

Additional embodiments of connectors may be employed in other embodiments of the present disclosure. For example, FIG. 12 illustrates an embodiment of the aerosol delivery device 600" wherein the control body 400" comprises a first connector portion 420" comprising a plurality of extensions **424*a-c*" respectively comprising one of a plurality of spring pins 434*a-c*", which may also be referred to as pogo pins. In this regard, the spring pins 434*a-c*"** may be spring-loaded so as to allow for firm engagement with corresponding terminals.

For example, as further illustrated in FIG. 12, the cartridge 500" may include a second connector portion 516" comprising first and second heating terminals **520*a*", 520*b*" and a control component terminal 504", which may be provided as rings and a center circle that may be separated from each other. The spring pins 434*a-c*" may be positioned to engage a respective one of the terminals 520*a*", 520*b*", 504" so as to form electrical connections therewith. Usage of spring pins may provide some or all of the benefits of the tip-ring-sleeve plug described above. Additionally, spring pins may be configured to endure a higher number of engagement and disengagement cycles due to the spring pins 434***a-c*" not sliding against the terminals 520*a*", 520*b*", 504" during contact therebetween.

Note that although the portions of the connectors have been described above as being attached to one of the cartridge and the control body, the configurations described above have been provided by way of example only. In this regard, the portions of the connectors may be reversed between the cartridge and the control body such that, for example, the cartridge includes an extension and the control body includes a receptacle. In this regard, it may be desirable to attach the cheaper and/or more durable portion of the connector to the control body, which may be reusable whereas the cartridge may be disposable in some embodiments.

In an additional embodiment a method for assembling an aerosol delivery device is provided. As illustrated in FIG. 13, the method may include forming a control body by inserting an electrical power source into a control body outer body and engaging a first connector portion with the control body outer body at operation 702. Further, the method may include forming a cartridge by inserting a reservoir and an atomizer into a cartridge outer body and engaging a second connector portion with the cartridge outer body, the reservoir being configured to contain an aerosol precursor composition and the atomizer being configured to heat the aerosol precursor composition received from the reservoir to produce an aerosol. The first connector portion and the second connector portion may be configured to releasably engage each other. One of the first connector portion and the second connector portion may comprise an extension and the other of the first connector portion and the second connector portion may comprise a receptacle configured to receive the extension. The extension may comprise a plurality of contact sections positioned along a longitudinal length thereof. The contact sections may be electrically insulated from one another by at least one spacer and may be configured to form an electrical connection with the receptacle.

In some embodiments of the method engaging the first connector portion with the control body outer body at operation 702 may include engaging a coupler with a flow tube and engaging the flow tube with the control body outer body. Engaging the second connector portion with the cartridge outer body at operation 704 may include engaging a base with the cartridge outer body. Forming the control body at operation 702 may further comprise engaging an O-ring with the coupler. The O-ring may be configured to engage an inner surface of the second connector portion.

In some embodiments forming the control body at operation 702 may further comprise inserting a flow sensor in the control body outer body. The coupler may define a pressure port configured to be in fluid communication with the cartridge when the first connector portion engages the second connector portion. The method may further include engaging a pressure tube with the flow sensor and with the coupler.

The method may further include engaging the extension with one of the coupler and the base and engaging the receptacle with the other of the coupler and the base. Engaging the extension with one of the coupler and the base and engaging the receptacle with the other of the coupler and the base may include centrally disposing the extension and the receptacle with respect to a respective one of the coupler and the base. Engaging the extension with one of the coupler and the base may include engaging a tip-ring-sleeve plug with one of the coupler and the base. The method may further include inserting a controller into the control body outer body and inserting an electronic control component into the cartridge outer body. Additionally, the method may include electrically coupling a data contact section of the extension with one of the controller and the electronic control component.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:

a control body including an electrical power source and a first connector portion; and a cartridge comprising:

a reservoir configured to contain an aerosol precursor composition;

an atomizer comprising a heating element configured to heat the aerosol precursor composition received from the reservoir to produce an aerosol; and a second connector portion, the first connector portion and the second connector portion being configured to releasably engage each other, the first connector portion comprising an extension electrically coupled to the electrical power source and the second connector portion comprising a receptacle configured to receive the extension, the receptacle comprising flexible heating terminals electrically coupled to the heating element of the atomizer and configured to form a mechanical connection with the extension by mechanically engaging a detent formed on the extension, the extension comprising a plurality of contact sections positioned along a longitudinal length thereof, the contact sections being electrically insulated from one another by at least one spacer and being configured to form an electrical connection with the receptacle, the receptacle being configured to receive electrical power from the extension.

2. The aerosol delivery device of claim 1, wherein the contact sections include a data contact section configured to form a data connection between the cartridge and the control body.

3. The aerosol delivery device of claim 1, wherein an air inlet is defined in the cartridge.

4. The aerosol delivery device of claim 3, wherein the first connector portion defines a pressure port configured to be in fluid communication with the air inlet when the first connector portion engages the second connector portion.

5. The aerosol delivery device of claim 1, wherein the first connector portion further comprises an O-ring configured to engage an inner surface of the second connector portion.

6. The aerosol delivery device of claim 1, wherein the extension comprises a tip-ring-sleeve plug.

7. The aerosol delivery device of claim 1, wherein the receptacle comprises a center pin terminal.

8. The aerosol delivery device of claim 1, wherein the extension and the receptacle are centrally disposed with respect to a respective one of the first connector portion and the second connector portion.

9. The aerosol delivery device of claim 8, wherein the extension is configured to engage the receptacle regardless of a relative rotational position of the cartridge with respect to the control body.

* * * * *